(12) United States Patent
Heidemann et al.

(10) Patent No.: US 8,846,956 B2
(45) Date of Patent: Sep. 30, 2014

(54) PROCESS FOR THE PREPARATION OF CIS-ROSE OXIDE

(71) Applicant: BASF SE, Ludwigshafen (DE)

(72) Inventors: Thomas Heidemann, Viernheim (DE); Lucia Königsmann, Stuttgart (DE)

(73) Assignee: BASF SE (DE)

( * ) Notice: Subject to any disclaimer, the term of this patent is extended or adjusted under 35 U.S.C. 154(b) by 99 days.

(21) Appl. No.: 13/661,858

(22) Filed: Oct. 26, 2012

(65) Prior Publication Data
US 2013/0109867 A1    May 2, 2013

Related U.S. Application Data

(60) Provisional application No. 61/552,469, filed on Oct. 28, 2011.

(51) Int. Cl.
*C07D 309/04* (2006.01)

(52) U.S. Cl.
CPC .................................... *C07D 309/04* (2013.01)
USPC ....................................................... 549/356

(58) Field of Classification Search
None
See application file for complete search history.

(56) References Cited

U.S. PATENT DOCUMENTS 8,546,591 B2 * 10/2013 Koenigsmann et al. ...... 549/356

FOREIGN PATENT DOCUMENTS

| EP | 0082401 A1 | 6/1983 |
| WO | WO-79/00509 A1 | 8/1979 |
| WO | WO-2009/077550 A1 | 6/2009 |

OTHER PUBLICATIONS

Tyman, et al., "The Reaction of 3-Alkene-1-Ols with Aldehydes: A Synthesis of (+)-Cis-2-(2'Methyl-1'-Propenyl)-4 Methyltetrahydropyran" Tetrahedron Letters, No. 51 (1970) pp. 4507-4508.

* cited by examiner

*Primary Examiner* — Sun Jae Yoo
(74) *Attorney, Agent, or Firm* — Drinker Biddle & Reath LLP

(57) ABSTRACT

The present invention relates to a process for the preparation of a composition enriched in cis-2-(2-methylprop-1-enyl)-4-methyltetrahydropyran, comprising the catalytic hydrogenation of 2-(2-methylprop-1-enyl)-4-methylenetetrahydropyran in the presence of hydrogen and a heterogeneous catalyst comprising ruthenium.

17 Claims, No Drawings

PROCESS FOR THE PREPARATION OF CIS-ROSE OXIDE

CROSS-REFERENCE TO RELATED APPLICATIONS

This application claims benefit under 35 U.S.C. §119(e) of U.S. Provisional Patent App. Ser. No. 61/552,469, filed Oct. 28, 2011, which is incorporated herein by reference in its entirety.

DESCRIPTION

The present invention relates to a process for the preparation of a composition enriched in cis-2-(2-methylprop-1-enyl)-4-methyltetrahydropyran comprising the catalytic hydrogenation of 2-(2-methylprop-1-enyl)-4-methylenetetrahydropyran in the presence of hydrogen and a heterogeneous catalyst comprising ruthenium.

Cis-2-(2-methylprop-1-enyl)-4-methyltetrahydropyran is a valuable aroma chemical also referred to as cis-rose oxide. It is usually produced in the form of a diastereomer mixture with the corresponding trans-configured compound, the cis-configured compound having proven to be the more valuable compound on account of having a better odor. Since the diastereomers can only be separated from one another with difficulty, especially when produced on an industrial scale, there is a continuing need for preparation processes in which the preferred cis-isomer of rose oxide is formed as selectively as possible in a high yield.

In Tetrahedron Letters No. 51, 4507-4508, 1970, J. H. P. Tyman and B. J. Willis describe the acid-catalyzed reaction of 3-alken-1-ols with aldehydes, specifically the reaction of 3-methyl-2-buten-1-al with 2-methyl-1-buten-4-ol and subsequent dehydration. The intermediate obtained in this way and having an exocyclic methylene group was hydrogenated under homogeneous catalysis in the presence of $SnCl_2$/$H_2PtCl_6$ to give the racemic cis-2-(2-methylprop-1-enyl)-4-methyltetrahydropyran.

WO 79/00509 discloses a process for the preparation of mixtures, enriched with regard to the cis isomer, of cis- and trans-(2-methylprop-1-enyl)-4-methyltetrahydropyran by catalytic hydrogenation of the corresponding precursor having an exo-methylene group in the 4 position. Raney-nickel and palladium catalysts, specifically palladium on carbon, are specified as suitable hydrogenation catalysts. The isomer enrichment is achieved by treating the hydrogenation product with an acidic or Lewis-acidic reagent. Boron trifluoride is specified as preferred Lewis acid. The hydrogenation described by way of example with Raney nickel with subsequent distillation produces a mixture of the cis and transisomers in a ratio of 4:6 in a yield of 87.9% of theory. This mixture is converted in the subsequent isomerization to an isomer mixture in the ratio of about 85:15 in a yield of 86.5% of theory.

EP 0 082 401 A1 discloses a process for the preparation of rose oxide comprising predominantly, i.e. to at least 85%, the cis isomer. The process comprises hydrogenating 2-[2-methylprop-1-enyl]-4-methylenetetrahydropyran ("dehydrorose oxide") over a platinum dioxide or a platinum/carbon catalyst in the presence of a strongly acidic cation exchanger. In the isomerizing hydrogenation described by way of example of dehydrorose oxide to rose oxide, a yield of up to 87% of theory with an isomer content of the trans isomer of 90.5% and of the cis isomer of 7% is achieved.

WO 2009/077550 describes a process for the preparation of cis-2-(2-methylprop-1-enyl)-4-methyltetrahydropyran, comprising the catalytic hydrogenation of 2-(2-methyl-prop-1-enyl)-4-methylenetetrahydropyran in the presence of hydrogen and a heterogeneous catalyst which comprises ruthenium on a carbon support, and subsequent isomerization to increase the fraction of cis isomer by bringing the compounds obtained in this way into contact with a strongly acidic cation exchanger. Although this process permits the preparation of rose oxide with good yields and selectivities, a further improvement in the catalytic hydrogenation is desirable.

Surprisingly, it has been found that by using a heterogeneous catalyst which comprises ruthenium on an aluminum oxide support, the selectivity of the hydrogenation can be again significantly improved. Moreover, the newly used catalyst can be subjected to a simpler activation, for which, moreover, an improved activity is achieved.

The invention therefore provides a process for the preparation of a composition enriched in cis-2-(2-methylprop-1-enyl)-4-methyltetrahydropyran, comprising the catalytic hydrogenation of 2-(2-methylprop-1-enyl)-4-methylenetetrahydropyran in the presence of hydrogen and a heterogeneous catalyst which comprises ruthenium on an aluminum oxide support.

Within the context of the invention, the term "rose oxide" refers to cis/trans mixtures of any composition and also the pure conformation isomers. Furthermore, the term "rose oxide" refers to all enantiomers in pure form and also to racemic and optically active mixtures of the enantiomers of rose oxide.

In a preferred embodiment, the process according to the invention relates to a process for the preparation of an isomer mixture of cis-2-(2-methylprop-1-enyl)-4-methyltetrahydropyran of the formula (IIa) and trans-2-(2-methylprop-1-enyl)-4-methyltetrahydropyran of the formula (IIb).

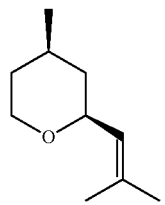

(IIa)

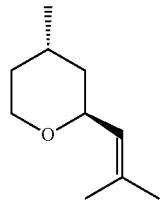

(IIb)

According to the invention, the compounds of the formulae (IIa) and (IIb) are produced in racemic form. Accordingly, the formula images (IIa) and (IIb) serve to illustrate the relative configuration of the two stereocenters and are in each case the racemic mixtures of the respective enantiomer pairs.

The 2-(2-methylprop-1-enyl)-4-methylenetetrahydropyran used as starting material can in principle be prepared in any manner, and no specific requirements are placed on its nature or purity which extend beyond the scope of that which is customary for synthetic purposes. Preferably, racemic 2-(2-methylprop-1-enyl)-4-methylenetetrahydropyran is used, as is shown by formula (I).

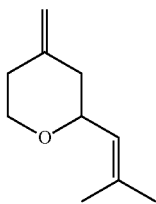

(I)

In a preferred embodiment, the process according to the invention comprises, as an additional, upstream process step, the preparation of 2-(2-methylprop-1-enyl)-4-methylenetetrahydropyran (dehydrorose oxide) of the formula (I) by reaction of 3-methylbut-3-en-1-ol (isoprenol) of the formula (III)

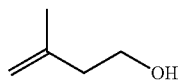

(III)

with 3-methylbut-2-en-1-al (prenal) of the formula (IV)

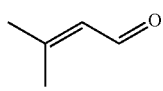

(IV)

in a condensation reaction. Details can be found below in the description relating to step i).

Within the context of the invention, a composition enriched in cis-2-(2-methylprop-1-enyl)-4-methyltetrahydropyran is understood as meaning a composition which comprises more than 50% by weight of cis-2-(2-methylprop-1-enyl)-4-methyltetrahydropyran, based on the total amount of cis and trans isomers in the composition.

In general, using the process according to the invention, it is possible to prepare compositions enriched in cis-2-(2-methylprop-1-enyl)-4-methyltetrahydropyran which comprise preferably at least 70% by weight, particularly preferably at least 80% by weight, in particular at least 90% by weight, of cis-2-(2-methylprop-1-enyl)-4-methyltetrahydropyran, based on the total amount of cis and trans isomers in the composition. Accordingly, the composition obtained by the process according to the invention comprises preferably at most 30% by weight, particularly preferably at most 20% by weight, in particular at most 10% by weight, of trans-2-(2-methylprop-1-enyl)-4-methyltetrahydropyran, based on the total amount of cis and trans isomers in the composition. In a specific embodiment, the composition obtained by the process according to the invention comprises 90 to 98% of cis-2-(2-methylprop-1-enyl)-4-methyltetrahydropyran and 2 to 10% by weight of trans-2-(2-methylprop-1-enyl)-4-methyltetrahydropyran, in each case based on the total amount of cis and trans isomers in the composition.

Preferably, the composition enriched in cis-2-(2-methylprop-1-enyl)-4-methyltetrahydropyran obtained by the process according to the invention comprises at most 10% by weight, particularly preferably at most 5% by weight, in particular at most 2% by weight, of compounds different from cis- and trans-2-(2-methylprop-1-enyl)-4-methyltetrahydropyran.

In the process according to the invention, a heterogeneous catalyst is used which comprises ruthenium on an aluminum oxide support.

Within the context of the invention, an aluminum oxide support is understood as meaning a support which consists to at least 50% by weight, based on the total weight of the support material, of aluminum oxide.

The support used according to the invention can comprise aluminum oxide in a mixture with other support materials. Suitable other support materials are selected for example from graphite, silicon dioxide, titanium dioxide, zirconium dioxide and mixtures thereof. As other support materials, preference is given to titanium dioxide and/or zirconium dioxide. Preferably, the support consists at least to 80% by weight, particularly preferably to at least 90% by weight, in particular to at least 96% by weight, based on the total weight of the support material, of aluminum oxide.

In the process according to the invention, particular preference is given to using a catalyst in which the aluminum oxide fraction of the support consists essentially of alpha-aluminum oxide.

The aluminum oxide fraction of the support consists preferably to at least 80% by weight, particularly preferably to at least 90% by weight, in particular to at least 98% by weight, of alpha-aluminum oxide, based on the total aluminum oxide fraction of the support. The phase composition of the support can be determined using XRD (X-ray diffraction).

The catalyst used according to the invention comprises ruthenium as active metal. Preferably, the catalyst comprises 0.001 to 10% by weight of ruthenium, particularly preferably 0.01 to 5% by weight, of ruthenium, in particular 1 to 3% by weight of ruthenium, based on the total weight of the catalyst.

The weight data with regard to ruthenium and other metals refer to the weight of the metal, although the metals are usually present in oxidic form on the support.

Additionally, the catalyst according to the invention can comprise at least one metal other than ruthenium as active metal or as promoter. Other active metals are preferably selected from the elements of groups 7 to 11 of the Periodic Table of the Elements.

The catalysts according to the invention can additionally comprise at least one other metal, preferably selected from copper, gold, palladium, platinum, osmium, iridium, silver, rhenium and mixtures thereof. Preferably, the catalyst comprises 0 to 10% by weight, preferably 0.001 to 5% by weight, specifically 0.01 to 1% by weight, of another metal, selected from copper, gold, palladium, platinum, osmium, iridium, silver, rhenium and mixtures thereof, based on the total weight of the catalyst.

Preferred other metals are copper and/or gold.

The catalysts can also comprise one or more other metals as promoters. The promoters are preferably selected from alkali metals, alkaline earth metals, rare earth metals, titanium, manganese, molybdenum, tin and mixtures thereof. These are usually present in an amount of from 0 to 10% by weight, based on the total weight of the catalyst. If the catalysts comprise one or more other metals as promoters, then these are preferably present in an amount of from 0.001 to 5% by weight, particularly preferably in an amount of from 0.1 to 3% by weight, based on the total weight of the catalyst.

The promoters are particularly preferably selected from lithium, sodium, potassium, rubidium, cesium, magnesium, calcium, strontium, barium, scandium, yttrium, lanthanum, cerium, praseodymium, neodymium, titanium, manganese, molybdenum, tin and mixtures thereof.

The promoters are selected in particular from lithium, sodium, potassium, magnesium, calcium, scandium, yttrium, lanthanum, cerium, titanium, manganese, molybdenum, tin and mixtures thereof.

The promoters are specifically selected from potassium, magnesium, lanthanum, cerium, titanium, manganese, molybdenum, tin and mixtures thereof.

Preferred catalysts according to the invention comprise
a) 0.001 to 10% by weight, preferably 1 to 3% by weight, of ruthenium,
b) 0 to 5% by weight, preferably 0 to 3% by weight, of one or more alkaline earth metals,
c) 0 to 5% by weight, preferably 0 to 3% by weight, of one or more alkali metals,
d) 0 to 10% by weight, preferably 0 to 3% by weight, of one or more rare earth metals,
e) 0 to 10% by weight, preferably 0 to 1% by weight, of one or more other metals selected from the group consisting of copper, gold, palladium, platinum, osmium, iridium, silver and rhenium,
in each case based on the total weight of the catalyst. The weight data refer to the weight of the metal, although the metals are usually present in oxidic form on the support.

A very particularly preferred active metal is ruthenium, which is generally present in amounts of from 0.001 to 10% by weight, based on the weight of the catalyst. In a specific embodiment, the catalyst according to the invention comprises 1 to 3% by weight, for example about 1.6% by weight, of ruthenium, on alpha-aluminum oxide as support and in addition no other active metals and promoter metals. Preferably, the ruthenium is present as RuO2.

The catalysts according to the invention can be prepared by customary processes known to the person skilled in the art. In a preferred embodiment, the catalysts are obtained by saturating the support material with aqueous solutions of salts of the metals. Metals other than gold are usually applied to the support as aqueous solutions of their chlorides, oxychlorides or oxides. The ruthenium catalysts can be obtained, for example, by saturating the support material with aqueous solutions of RuCl3, optionally the salt of at least one other active metal and/or optionally a promoter for the doping. Preferably, the chlorides are used in each case. The shaping of the catalyst can take place after or preferably before the impregnation of the support material.

The catalysts according to the invention can be used in powder form. Catalysts of this type preferably have an average particle size in a range from 10 to 200 μm. Pulverulent catalysts are preferably suitable for use in the fluidized bed.

The catalysts according to the invention can also be used in the form of catalyst moldings. Catalyst moldings are preferably suitable for use as fixed-bed catalysts.

The moldings or powders can be dried and optionally calcined after the impregnation at elevated temperatures. The temperature during drying and/or calcination is preferably in a range from 50 to 600° C., particularly preferably from 100 to 400° C.

The drying of the impregnated catalyst moldings can take place continuously or batchwise, e.g. in belt or tray furnaces. The drying can take place at atmospheric pressure or reduced pressure. Furthermore, the drying can take place in a gas stream, e.g. an air stream or a nitrogen stream. In general, the drying is carried out at temperatures of from 50 to 200° C., preferably 100 to 150° C.

The calcination of the optionally pre-dried catalyst takes place generally at temperatures of from 150 to 600° C., preferably 200 to 400° C. The calcination can be carried out continuously or batchwise, e.g. in belt or tray furnaces. The calcination can take place at atmospheric pressure or reduced pressure and/or in a gas stream, e.g. in an inert-gas stream, oxygen-containing gas stream, or hydrogen-containing gas stream. Suitable inert gases are e.g. nitrogen or argon. In the case of calcination in an oxygen-containing atmosphere, the chlorides produce the oxides, such as, for example, RuO2. A pretreatment with hydrogen or hydrogen-comprising gases generally serves for the prereduction/activation of the hydrogenation catalyst.

The shaping to give shaped catalyst particles can take before or after the impregnation.

Suitable catalyst moldings are any desired forms, preference being given to tablets, rings, cylinders, stars, cartwheels or balls, particular preference being given to rings, cylinders or star strands.

The specific surface area of the alpha-aluminum oxide support prior to the metal salt deposition is generally in the range from 0.1 to 10 m$^2$/g. Alpha-aluminum oxide can be prepared by heating gamma-aluminum oxide to temperatures above 1000° C., and it is preferably prepared in this way. In general, calcination lasts 2 to 24 h.

Ruthenium catalysts suitable for the process according to the invention and processes for their preparation are described in WO 2007/023162, to which reference is made here in its entirety.

In a preferred embodiment of the process according to the invention, prior to being used for the catalytic hydrogenation of 2-(2-methylprop-1-enyl)-4-methylenetetrahydropyran, the catalyst is subjected to a reduction at elevated temperatures in the presence of a hydrogen-containing gas.

Pure hydrogen can be used for the reduction. For the reduction, preference is given to using a hydrogen-containing gas which comprises hydrogen in a mixture with at least one inert gas. Suitable inert gases are, for example, nitrogen, argon or helium. Preferably, the hydrogen content of the hydrogen-containing gas is at most 80% by volume, particularly preferably at most 60% by volume. Preferably, the hydrogen content of the hydrogen-containing gas is in a range from 10 to 60% by volume.

In a preferred embodiment, the reduced catalyst is placed directly after the reduction into an inert liquid, where it is stored until it is used for the hydrogenation. Suitable inert liquids are the solvents suitable for carrying out the hydrogenation that are specified below. Preference is given to using water.

The hydrogenation of the 2-(2-methylprop-1-enyl)-4-methylenetetrahydropyran takes place preferably at a temperature in a range from 50 to 150° C., particularly preferably from 70 to 130° C.

The hydrogenation of the 2-(2-methylprop-1-enyl)-4methylenetetrahydropyran takes place preferably at an absolute pressure in a range from 1 to 50 bar, particularly preferably from 1.5 to 25 bar, in particular from 2 to 10 bar.

The hydrogenation of the 2-(2-methylprop-1-enyl)-4-methylenetetrahydropyran can take place in the presence of a solvent that is inert under hydrogenation conditions. Suitable solvents are, for example, water, alcohols, such as methanol, ethanol, n-propanol and isopropanol, aliphatic hydrocarbons and hydrocarbon mixtures, such as hexane, petroleum ether and ligroin, cyclic ethers, such as tetrahydrofuran.

The hydrogen used for the hydrogenation can be used in pure form or, if desired, also in the form of mixtures with other, preferably inert gases, such as nitrogen or argon. Preference is given to using hydrogen in undiluted form.

The conversion during the hydrogenation, based on rose oxide, is preferably at least 90%, in particular at least 94%.

The selectivity during the hydrogenation, based on rose oxide, is preferably at least 91%, particularly preferably at least 95%. In many cases, even higher selectivities of up to 96% and above can be achieved.

After separating off the catalyst used, for example by filtration, and optional removal of the solvent used, preferably by distillation, a reaction mixture is obtained which comprises the diastereomeric compounds of the formulae (IIa) and (IIb) and optionally also other impurities, undesired secondary components and also remains of unreacted starting material.

A preferred embodiment of the process according to the invention is a process in which i) a starting material comprising a 2-(2-methylprop-1-enyl)-4-methylenetetrahydropyran of the formula (I)

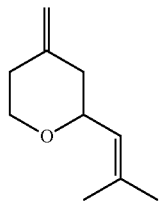
(I)

is prepared, ii) the starting material prepared in step i) is subjected to a catalytic hydrogenation in the presence of hydrogen and a heterogeneous catalyst comprising ruthenium on an aluminum oxide support, giving a reaction mixture comprising cis-2-(2-methylprop-1-enyl)-4-methyltetrahydropyran (IIa) and trans-2-(2-methylprop-1-enyl)-4-methyltetrahydropyran (IIb)

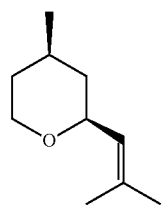
(IIa)

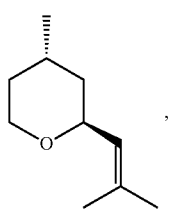
(IIb)

iii) optionally the compounds (IIa) and (IIb) are separated off from the reaction mixture obtained in step ii), and iv) the reaction mixture obtained in step ii) or the compounds (IIa) and (IIb) separated off in step iii) are brought into contact with a strong acidic ion exchanger, the transcompound (IIb) being isomerized at least partially into the cis compound (IIa).

Step i)

Preferably, the preparation of the starting mixture comprising 2-(2-methylprop-1-enyl)-4-methylenetetrahydropyran of the formula (I) in step i) comprises the reaction of 3-methylbut-3-en-1-ol (isoprenol) of the formula (III)

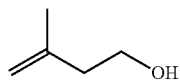
(III)

with 3-methylbut-2-en-1-al (prenal) of the formula (IV)

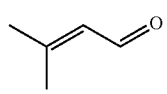
(IV)

in a condensation reaction.

Preferably, the reaction of 3-methylbut-3-en-1-ol (isoprenol) of the formula (III) with 3-methylbut-2-en-1-al (prenal) of the formula (IV) takes place in the presence of an acid and in the presence of a solvent which forms an azeotrope with water.

Preferably, here, the procedure involves separating off the water released during the aforementioned reaction of 3-methylbut-3-en-1-ol of the formula (III) with 3-methyl-but-2-en-1-al of the formula (IV) from the reaction mixture by azeotropic distillation with the solvent used. In this connection, it is possible to use either individual solvents which form an azeotrope with water or mixtures of different solvents. For this, preference is given to using those solvents which form an azeotrope with water which has a lower boiling point than the particular solvent or solvent mixture itself, preferably those whose azeotropic boiling point is in the range from about 60° C. to about 120° C., particularly preferably in the range from about 65° C. to about 90° C. Preferred solvents are selected from ethanol, benzene, tetrachloromethane, ethyl acetate, toluene, chloroform, n-heptane, cyclohexane, and methylcyclohexane. Particularly preferred solvents which form an azeotrope with water are selected from toluene, chloroform, n-heptane, cyclohexane, and methylcyclohexane. Very particularly preferred solvents are toluene and n-heptane. Toluene is especially preferred.

The separating off of the water released during the reaction by azeotropic distillation can be carried out by methods known per se to the person skilled in the art and/or using the devices suitable for this purpose, such as, for example, using a water separator.

The amount of solvent to be used within the context of the aforementioned azeotropic distillation can be chosen within a wide range and is usually governed by the chosen reaction conditions and also the device used for separating off the water. It has proven to be advantageous to use the solvent in a quantitative ratio, based on the total amount of the starting materials 3-methylbut-3-en-1-ol (III) and 3-methylbut-2-en-1-al (IV) used, of from about 1:1 to about 2:1, particularly preferably about 1:1 to about 1.5:1. After carrying out the reaction, the solvent can generally be separated off easily and can be reused in the course of further reactions.

The provision of dehydrorose oxide of the formula (I) by reacting 3-methylbut-3-en-1-ol (III) and 3-methylbut-2-en-1-al (IV) is preferably carried out in the presence of an acid. Suitable acids are both organic and inorganic acids, such as, for example p-toluene-sulfonic acid, trifluoroacetic acid or alkali metal hydrogensulfates. In a preferred embodiment, the reaction of 3-methylbut-3-en-1-ol (III) with 3-methylbut-2-en-1-al (IV) is carried out in the presence of an alkali metal hydrogensulfate, such as, for example sodium hydrogensulfate or potassium hydrogensulfate. Preference is given to sodium hydrogensulfate.

The selected acid is preferably used in catalytic amounts, usually, based on the total amount of the starting materials 3-methylbut-3-en-1-ol (III) and 3-methylbut-2-en-1-al (IV) to be reacted, in an amount of from about 0.01 to about 1% by weight.

The reaction to prepare dehydrorose oxide by condensation of isoprenol with prenal is carried out usually, and depending on the selected solvent or solvent mixture and the selected acid, at temperatures in the range from about 60° C. to 150° C., preferably in the range from about 70° C. to 120° C. and is then as a rule largely concluded rapidly, often after about 24 h or even earlier. The reaction mixture obtained can be worked up by methods known to the person skilled in the art, for example by extractive methods, optionally following neutralization of the acid used. The dehydrorose oxide of the formula (I) thus obtained as crude product can then be further purified, for example by chromatography or preferably by (fractional) distillation, during which in particular the nerol oxide usually produced as by-product and also further high-boiling secondary components can be separated off.

Step ii

As regards suitable and preferred embodiments in respect of step ii), reference is made in full to the previous statements relating to the catalytic hydrogenation of 2-(2-methyl-prop-1-enyl)-4-methylenetetrahydropyran in the presence of hydrogen and a heterogeneous catalyst comprising ruthenium on an aluminum oxide support.

Step iii)

According to process step iii), to be optionally carried out, of the process according to the invention, a separating off of the compounds of the formulae (IIa) and (IIb) from the reaction mixture obtained according to step ii) can be carried out if desired. For this purpose, the methods of material separation which appear suitable to the person skilled in the art are available, such as, for example chromatography or preferably distillation. Suitable distillation apparatuses include, for example, devices for short-path distillation, such as, for example, thin-film evaporators or else filled or packed columns, and also plate columns.

Step iv)

The mixture of the compounds of the formula (IIa) and (IIIb), obtained in this way according to process step ii) or following purification according to the optional process step iii), is then brought into contact, in process step iv), with a strongly acidic cation exchanger, with at least partial isomerization of the transcompound of the formula (IIb) to give the ciscompound of the formula (IIa).

After carrying out process step iv), mixtures of the compounds of the formulae (IIa) and (IIb) are obtained which have a higher content of the desired compound of the formula (IIa) than the mixtures initially obtained by process step ii) and/or iii). In this way, preferably the aforementioned diastereomer-enriched mixtures of cis-2-(2-methylprop-1-enyl)-4-methyltetrahydropyran of the formula (IIa) and trans-2-(2-methylprop-1-enyl)-4-methyltetrahydropyran of the formula (IIb) are obtained, comprising, based on the amount of the isomer mixture, at least 70%, preferably at least 90% and particularly preferably 90 to 98% of cis-2-(2-methylprop-1-enyl)-4-methyltetrahydropyran of the formula (I) and at most 30%, preferably at most 10% and particularly preferably 2 to 10% of trans-2-(2-methylprop-1-enyl)-4-methyltetrahydropyran of the formula (IIb).

The isomerization according to process step iv) of the process according to the invention takes place in the presence of a strongly acidic ion exchanger, i.e. a strongly acidic cation exchanger such as, for example, Lewatit® S100, Lewatit® SP1 12, Lewatit® S115, Lewatit® SP1080, Lewatit® SC102, Lewatit® SPC118, Lewatit® CNP 80, Lewatit® HD 5, Amberlite® IR 120, Amberlite® R200, Amberlyst® 15, Bay. KAT. K 2431, Bay. KAT. K 2621, Dowex® 50, Permutit® RS, Wofatit® KPS 200, Duolite® C-3, Duolite® C-10, Duolite®C-25, Wofatit® F, Wofatit® D, Wofatit® P, Zeoxex (Zeokarb H), Nalcite NCR, Nalcite HGR, Nalcite HDR, Permutit® Q and Permutit® RS, Serdrolit® Red. The selected strongly acidic cation exchangers can also be used in the form of mixtures of two or more different cation exchangers. Preference is given to using the cation exchangers Lewatit® SP1 12 and/or Amberlyst® 15.

Within the context of a preferred embodiment of the process according to the invention, the selected cation exchanger is used in the form of a fixed bed, via which the diastereomer mixture, obtained from process step ii) or iii), to be reacted is passed as such or in the form of a solution in a suitable solvent which is inert under the reaction conditions. Preferably, the mixture to be isomerized is brought into contact in undiluted form with the selected, strongly acidic cation exchanger. In this connection, the fixed bed can be arranged, for example, in the form of a bed of the selected cation exchanger in a reactor tube, with the mixture to be isomerized being passed through the reactor tube filled in this way. For this purpose, the reactors can be operated in all operating and processing modes which are considered suitable to a person skilled in the art, such as, for example, in liquid-phase mode or, preferably according to the invention, in trickle mode, where the mixture to be isomerized is trickled onto a bed of the selected cation exchanger.

In this way, the continuous reaction procedure preferred according to the invention within the context of process step iv) is also possible. In the context of a preferred embodiment, process step iv) is therefore carried out continuously. In this way, the mixture comprising the compounds of the formula (IIa) and (IIb) that is to be isomerized is fed continuously to the cation exchanger, for example by introduction into a reactor filled with cation exchanger, and continuously removed again from same, for example by discharge of the isomerized mixture from the reactor.

The mixture of the compounds of the formulae (IIa) and (IIb) to be isomerized can also be repeatedly brought into contact one after the other with the selected strongly acidic cation exchanger or else with different strongly acidic cation exchangers, for example by returning the diastereomer-enriched isomer mixture discharged from the fixed-bed reactor as described above to the same reactor. It is also possible to pass through several such reactors, which may, if desired, also be filled with different cation exchangers, one after the other in order, in so doing, to arrive at the desired diastereomer ratio as described above.

The isomerization according to process step iv) is usually carried out at temperatures of from about 0° C. to about 100° C., preferably at about 20 to about 80° C.

The examples below serve to illustrate the invention without limiting it in any way.

EXAMPLES

Example 1

Preparation of Dehydrorose Oxide

Analogous to WO 2009/077550, Example 1

In a reaction vessel with a volume of 5 l and provided with stirrer, water separator, condenser and a metering pump, 2000 g of toluene and 1.5 g of NaHSO4 (as 10% strength aqueous solution) were initially introduced and 7.67 mol (660 g) of 3-methylbut-3-en-1-ol and 7.67 mol (643.5 g) of 3-methylbut-2-en-1-al were metered in over the course of 16 h at 110-115° C. The water was continuously discharged from the reaction mixture with toluene and the toluene was returned. The reaction mixture was then stirred for a further 5.5 h at 115° C. The resulting reaction mixture was then washed with 278 g of 2% strength NaOH solution. The toluene was distilled off at a pressure of 200 mbar over a 30 cm-long column, filled with Raschig rings. The conversion to dehydrorose oxide (DHR) was 62.7% of theory. Finally the DHR was separated from nerol oxide and high-boiling secondary components by distillation and obtained with a purity of >99%.

Example 2 (According to the Invention)

Firstly, a RuO2 catalyst on an alpha-Al2O3 support was prepared according to example 1 of WO 2007/023161. For this purpose, a pulverulent gamma-aluminum oxide support from Sasol (Puralox (R) SCCa 30/170) was firstly converted to alpha-$Al_2O_3$. The support consists of particles with an average particle diameter of ca 50 pm. 2000 g of the Puralox (R) SCCa 30/170 were heat-treated at 1200 to 1300° C. for 5 h. 1500 g of the support obtained were impregnated with an aqueous $RuCl_3$ hydrate solution (55.56 g of RuCl3 hydrate, corresponding to 41.8% by weight of Ru in 480 g of water). The water absorption of the support was ca 0.38 ml/g. After the impregnation with 90% water absorption, the impregnated support was dried at 120° C. for 6 h and then calcined at 350° C. for 2 h. The catalyst produced in this way comprised ca 2% $RuO_2$ on alpha-$Al_2O_3$. The catalyst was then firstly reduced at 200° C. in a dilute hydrogen stream (50% by volume $H_2$, 50% by volume N2) and, after cooling by means of rinsing with degassed water, charged to a storage vessel.

7.3 g (=0.11 g of Ru) of this catalyst (calculated on a dry basis) and 220 g of dehydrorose oxide from example 1 were charged to a 500 ml Büchl laboratory autoclave and converted to rose oxide at a hydrogen pressure of 4 bar absolute and a temperature of 70° C. After a reaction time of 4 hours, the conversion was 94% and the selectivity to rose oxide was 96%.

Example 3 (Comparison)

Analogous to WO 2009/077550, Example 2

A catalyst as in example 1 of EP 0071787 was used which comprises 5% by weight of Ru and 1% by weight of Fe on an activated carbon support.

2.2 g (=0.11 g of Ru) of this catalyst (calculated on a dry basis) and 220 g of dehydrorose oxide from example 1 were charged to a 500 ml Buchi laboratory autoclave and converted to rose oxide at a hydrogen pressure of 4 bar absolute and a temperature of 70° C. After a reaction time of 5 hours, the conversion was 93% and the selectivity to rose oxide was 90%.

The invention claimed is:

1. A process for the preparation of a composition enriched in cis-2-(2-methylprop-1-enyl)-4-methyltetrahydropyran comprising the catalytic hydrogenation of 2-(2-methylprop-1-enyl)-4-methylenetetrahydropyran in the presence of hydrogen and a heterogeneous catalyst comprising ruthenium on an aluminum oxide support.

2. The process according to claim 1, wherein the aluminum oxide support consists to at least 80% by weight, based on the total weight of the support material, of aluminum oxide.

3. The process according to claim 1, wherein the aluminum oxide support consists to at least 80% by weight, of alpha-aluminum oxide, based on the total aluminum oxide fraction of the support.

4. The process according to claim 1, wherein a catalyst is used which comprises 0.001 to 10% by weight of ruthenium, based on the total weight of the catalyst.

5. The process according to claim 1, wherein a catalyst is used which comprises
  a) 0.001 to 10% by weight of ruthenium,
  b) 0 to 5% by weight of one or more alkaline earth metals,
  c) 0 to 5% by weight of one or more alkali metals,
  d) 0 to 10% by weight of one or more rare earth metals,
  e) 0 to 10% by weight of one or more further metals selected from the group consisting of copper, gold, palladium, platinum, osmium, iridium, silver and rhenium,
  in each case based on the total weight of the catalyst.

6. The process according to claim 1, wherein a catalyst is used which comprises, as the sole metal component, 1 to 3% by weight of ruthenium in the form of RuO2 on an alpha-aluminum oxide support.

7. The process according to claim 1, wherein the catalyst is subjected, prior to being used for the catalytic hydrogenation of 2-(2-methylprop-1-enyl)-4-methylenetetrahydropyran, to a reduction at elevated temperatures in the presence of a hydrogen-containing gas.

8. The process according to claim 1, in which
  i) a starting material comprising 2-(2-methylprop-1-enyl)-4-methylenetetrahydropyran of the formula (I)

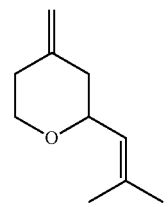

(I)

is prepared, ii) the starting material prepared in step i) is subjected to a catalytic hydrogenation in the presence of hydrogen and a heterogeneous catalyst comprising ruthenium on an aluminum oxide support, giving a reaction mixture comprising cis-2-(2-methylprop-1-enyl)-4-methyltetrahydropyran (IIa) and trans-2-(2-methylprop-1-enyl)-4-methyltetrahydropyran (IIb)

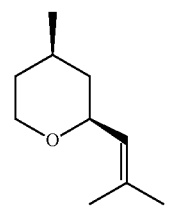

(IIa)

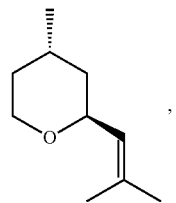

(IIb)

iii) optionally the compounds (IIa) and (IIb) are separated off from the reaction mixture obtained in step ii), and iv) the reaction mixture obtained in step ii) or the compounds (IIa) and (IIb) separated off in step iii) are brought into contact with a strong acidic ion exchanger, the transcompound (IIb) being isomerized at least partially into the cis compound (IIa).

9. The process according to claim 8, wherein the preparation of the starting mixture comprising 2-(2-methylprop-1-enyl)-4-methylenetetrahydropyran of the formula (I) in step i) comprises the reaction of 3-methylbut-3-en-1-ol of the formula (III)

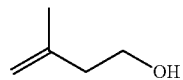

(III)

with 3-methylbut-2-en-1-al of the formula (IV)

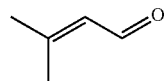

(IV)

in a condensation reaction.

10. The process according to claim 9, wherein the reaction of 3-methylbut-3-en-1-ol of the formula (III) with 3-methylbut-2-en-1-al of the formula (IV) takes place in the presence of an acid and a solvent which forms an azeotrope with water.

11. The process according to claim 10, wherein the water released during the reaction of 3-methylbut-3-en-1-ol of the formula (III) with 3-methylbut-2-en-1-al of the formula (IV) is separated from the reaction mixture by azeotropic distillation with the solvent used.

12. The process according to claim 1, wherein the aluminum oxide support consists to at least 90% by weight based on the total weight of the support material, of aluminum oxide.

13. The process according to claim 1, wherein the aluminum oxide support consists to at least 96% by weight based on the total weight of the support material, of aluminum oxide.

14. The process according to claim 1, wherein the aluminum oxide support consists to at least 90% by weight of alpha-aluminum oxide, based on the total aluminum oxide fraction of the support.

15. The process according to claim 1, wherein the aluminum oxide support consists to at least 98% by weight of alpha-aluminum oxide, based on the total aluminum oxide fraction of the support.

16. The process according to claim 1, wherein a catalyst is used which comprises 00.01 to 5% by weight of ruthenium, based on the total weight of the catalyst.

17. The process according to claim 1, wherein a catalyst is used which comprises 1 to 3% by weight of ruthenium, based on the total weight of the catalyst.

* * * * *